(12) United States Patent
Slaker et al.

(10) Patent No.: US 9,511,185 B2
(45) Date of Patent: Dec. 6, 2016

(54) INTRAVENOUS LINE LIFTER DEVICES, SYSTEMS AND METHODS

(71) Applicant: Regents of the University of Minnesota, Minneapolis, MN (US)

(72) Inventors: Bradley F. Slaker, Loretto, MN (US); Teresa Herriage, Minneapolis, MN (US); Mary C. Hooke, Eden Prairie, MN (US); Larry Goss, St. Louis Park, MN (US)

(73) Assignees: REGENTS OF THE UNIVERSITY OF MINNESOTA, Minneapolis, MN (US); DESIGNWISE MEDICAL, INC., Loretto, MN (US)

( * ) Notice: Subject to any disclaimer, the term of this patent is extended or adjusted under 35 U.S.C. 154(b) by 0 days.

(21) Appl. No.: 14/472,894

(22) Filed: Aug. 29, 2014

(65) Prior Publication Data

US 2015/0297826 A1     Oct. 22, 2015

Related U.S. Application Data

(60) Provisional application No. 61/981,567, filed on Apr. 18, 2014.

(51) Int. Cl.
| | | |
|---|---|---|
| *F16M 13/00* | (2006.01) | |
| *A61M 5/14* | (2006.01) | |
| *F16M 13/02* | (2006.01) | |
| *F16B 2/06* | (2006.01) | |

(52) U.S. Cl.
CPC ......... *A61M 5/1418* (2013.01); *F16M 13/022* (2013.01); *F16B 2/065* (2013.01)

(58) Field of Classification Search
USPC ........................................................ 248/560
See application file for complete search history.

(56) References Cited

U.S. PATENT DOCUMENTS

| | | | | | |
|---|---|---|---|---|---|
| 1,865,757 | A | * | 7/1932 | Honsowetz | A47C 21/00 211/119.006 |
| 2,470,524 | A | * | 5/1949 | Scudder | A61M 5/1415 248/122.1 |
| 2,593,567 | A | * | 4/1952 | Keck | A47C 21/00 211/119.006 |
| 2,607,881 | A | * | 8/1952 | Anderson | F21V 21/14 248/231.71 |
| 2,696,963 | A | * | 12/1954 | Shepherd | A61M 5/1415 24/339 |
| 2,913,740 | A | * | 11/1959 | Eldridge | A61G 7/0503 174/135 |

(Continued)

OTHER PUBLICATIONS

Simplicty, IV Management System, Innovative Medical Designs, available at www.imdusa.net, © 2010, 6 pages.

(Continued)

*Primary Examiner* — Monica Millner
(74) *Attorney, Agent, or Firm* — Patterson Thuente Pedersen, P.A.

(57) ABSTRACT

An intravenous line lifter system for supporting one or more IV lines that extend between a patient and patient care equipment is disclosed. The system can include a first elongated support member couplable to a support for the patient care equipment, a second elongated support member coupled to the first elongated support member, a first line retention device coupled to the first elongated support member, and a second line retention device coupled to the second elongated support member proximate the second end of the second elongated support member.

20 Claims, 18 Drawing Sheets

(56) References Cited

U.S. PATENT DOCUMENTS

| | | | | |
|---|---|---|---|---|
| 2,957,187 | A * | 10/1960 | Raia | A61G 7/0503 108/146 |
| 2,982,572 | A * | 5/1961 | Farber | F16B 7/0446 248/159 |
| 3,298,648 | A * | 1/1967 | Sepanski | A61J 9/06 248/103 |
| 3,460,789 | A * | 8/1969 | Engelsher | A61M 5/1415 211/113 |
| 3,709,372 | A * | 1/1973 | Alexander | A61M 5/1415 211/74 |
| 3,709,556 | A * | 1/1973 | Allard | A61G 5/10 248/125.1 |
| 3,835,486 | A * | 9/1974 | Benoit | A61G 7/0503 248/161 |
| 3,866,869 | A | 2/1975 | Woods | |
| 3,966,160 | A * | 6/1976 | Wilson | A61M 5/1417 248/297.51 |
| 4,225,104 | A * | 9/1980 | Larson | A61G 7/0503 16/422 |
| 4,541,596 | A * | 9/1985 | Price | A61M 5/1415 248/125.8 |
| 4,666,111 | A * | 5/1987 | Schuler | A61M 5/1415 248/125.1 |
| 4,744,536 | A * | 5/1988 | Bancalari | A61M 5/1415 248/125.8 |
| 4,875,651 | A * | 10/1989 | Wergin | A61G 13/101 248/291.1 |
| 4,905,944 | A * | 3/1990 | Jost | A61M 5/1415 248/125.8 |
| 4,988,062 | A * | 1/1991 | London | A61G 7/0503 128/DIG. 26 |
| 5,219,139 | A * | 6/1993 | Hertzler | A61G 5/10 248/276.1 |
| 5,236,213 | A * | 8/1993 | Trickett | A61G 5/10 248/276.1 |
| 5,279,486 | A * | 1/1994 | Harmon | A61G 7/075 248/122.1 |
| 5,288,093 | A * | 2/1994 | Gross | A61G 5/10 248/230.6 |
| 5,316,246 | A * | 5/1994 | Scott | A61M 5/1418 248/68.1 |
| 5,344,169 | A * | 9/1994 | Pryor | A61G 7/0503 248/129 |
| 5,421,548 | A * | 6/1995 | Bennett | A61G 5/10 248/129 |
| 5,470,037 | A * | 11/1995 | Willis | A61G 7/0503 248/125.9 |
| 5,699,988 | A * | 12/1997 | Boettger | A61G 5/10 248/122.1 |
| 5,735,806 | A * | 4/1998 | Leibovic | A61F 5/04 128/878 |
| 5,876,016 | A * | 3/1999 | Urban | A61M 3/0266 248/159 |
| 6,079,678 | A * | 6/2000 | Schott | A61G 7/05 248/125.1 |
| 6,224,026 | B1 * | 5/2001 | Dubois | F16M 11/04 248/118.3 |
| 6,315,759 | B1 * | 11/2001 | Peterson | A61M 5/14 248/68.1 |
| 6,375,133 | B1 * | 4/2002 | Morrow | A61M 5/1415 248/125.8 |
| 6,382,568 | B1 * | 5/2002 | Snell | F16L 3/22 128/DIG. 26 |
| 6,431,505 | B2 * | 8/2002 | Chinn | 248/121 |
| 6,458,104 | B2 * | 10/2002 | Gautsche | A61B 19/10 128/DIG. 26 |
| 6,698,044 | B2 * | 3/2004 | Limpert | A61F 5/3776 248/104 |
| 6,811,541 | B2 * | 11/2004 | Lambert | A61F 5/04 602/32 |
| 7,013,840 | B2 | 3/2006 | Leon | |
| 7,303,527 | B2 * | 12/2007 | Ng | A61B 1/303 248/124.1 |
| 7,533,428 | B2 * | 5/2009 | Yunker | A61M 5/1415 248/125.8 |
| 7,546,993 | B1 * | 6/2009 | Walker | A61M 5/1415 248/218.4 |
| 7,731,136 | B1 * | 6/2010 | Chisolm | A61M 5/1415 211/204 |
| 7,731,138 | B2 * | 6/2010 | Wiesner | A61M 5/1415 248/160 |
| 7,766,289 | B2 | 8/2010 | Newkirk | |
| 7,789,361 | B2 * | 9/2010 | Bally | A61G 7/05 248/124.2 |
| 7,896,298 | B2 * | 3/2011 | Meyers | A61M 5/1415 248/124.1 |
| 8,038,330 | B2 * | 10/2011 | Liu | F21V 21/06 248/125.8 |
| 8,100,371 | B2 * | 1/2012 | Eggleston | A61G 12/008 248/125.8 |
| 8,152,181 | B2 * | 4/2012 | Tomlinson | A61H 3/04 280/47.34 |
| 8,361,040 | B2 * | 1/2013 | Spohn | A61M 5/007 604/174 |
| 8,370,977 | B2 * | 2/2013 | Newkirk | A61G 7/018 248/176.1 |
| 8,460,272 | B2 | 6/2013 | Kudo | |
| 8,567,730 | B1 * | 10/2013 | Stevenson | A61M 5/1415 248/125.8 |
| 8,733,719 | B2 * | 5/2014 | Gaal | A61M 5/1415 248/218.4 |
| 8,739,335 | B1 * | 6/2014 | Hoggatt | A61G 1/013 5/503.1 |
| 8,863,333 | B2 * | 10/2014 | Cain | A61G 1/013 5/626 |
| 2002/0011543 | A1 * | 1/2002 | Chinn | A61M 5/1415 248/121 |
| 2002/0104934 | A1 * | 8/2002 | Elliott | A61M 5/1415 248/126 |
| 2002/0162926 | A1 * | 11/2002 | Nguyen | A61G 13/101 248/229.25 |
| 2004/0104321 | A1 * | 6/2004 | Marsolais | A61G 5/10 248/125.8 |
| 2004/0118982 | A1 * | 6/2004 | Shillings | F16L 3/223 248/68.1 |
| 2006/0230540 | A1 * | 10/2006 | Whelan | A61G 7/053 5/662 |
| 2006/0249635 | A1 | 11/2006 | Newkirk | |
| 2006/0253109 | A1 * | 11/2006 | Chu | A61B 17/0206 606/1 |
| 2007/0045481 | A1 * | 3/2007 | Adams | A61G 7/0503 248/59 |
| 2009/0019678 | A1 | 1/2009 | Taylor | |
| 2010/0146702 | A1 * | 6/2010 | Sherman | A47C 21/00 5/503.1 |
| 2011/0121149 | A1 * | 5/2011 | Herskovic | A61G 7/0503 248/223.41 |
| 2014/0191103 | A1 * | 7/2014 | Simon | F16M 13/022 248/558 |

OTHER PUBLICATIONS

MarketLab, IV Line Holder, available at http://www.marketlab.com/iv-line-holder/p/IVLineHolder as of Jan. 8, 2016, 1 page.

Springer America, Springer Product Specifications, available at www.springeramerica.com/product_specs.asp, dated Apr. 7, 2014, 1 page.

MarketLab, Boa I.V. Line Organizer, 1 page, as available at http://www.pr.com/press-release/202957, as of Feb. 2, 2016.

Advent Medical Technologies, Koala Klip Medical Tube & IV Line Organizer (Box of 100), Model: KK1000, dated Mar. 11, 2011, 1 page.

* cited by examiner

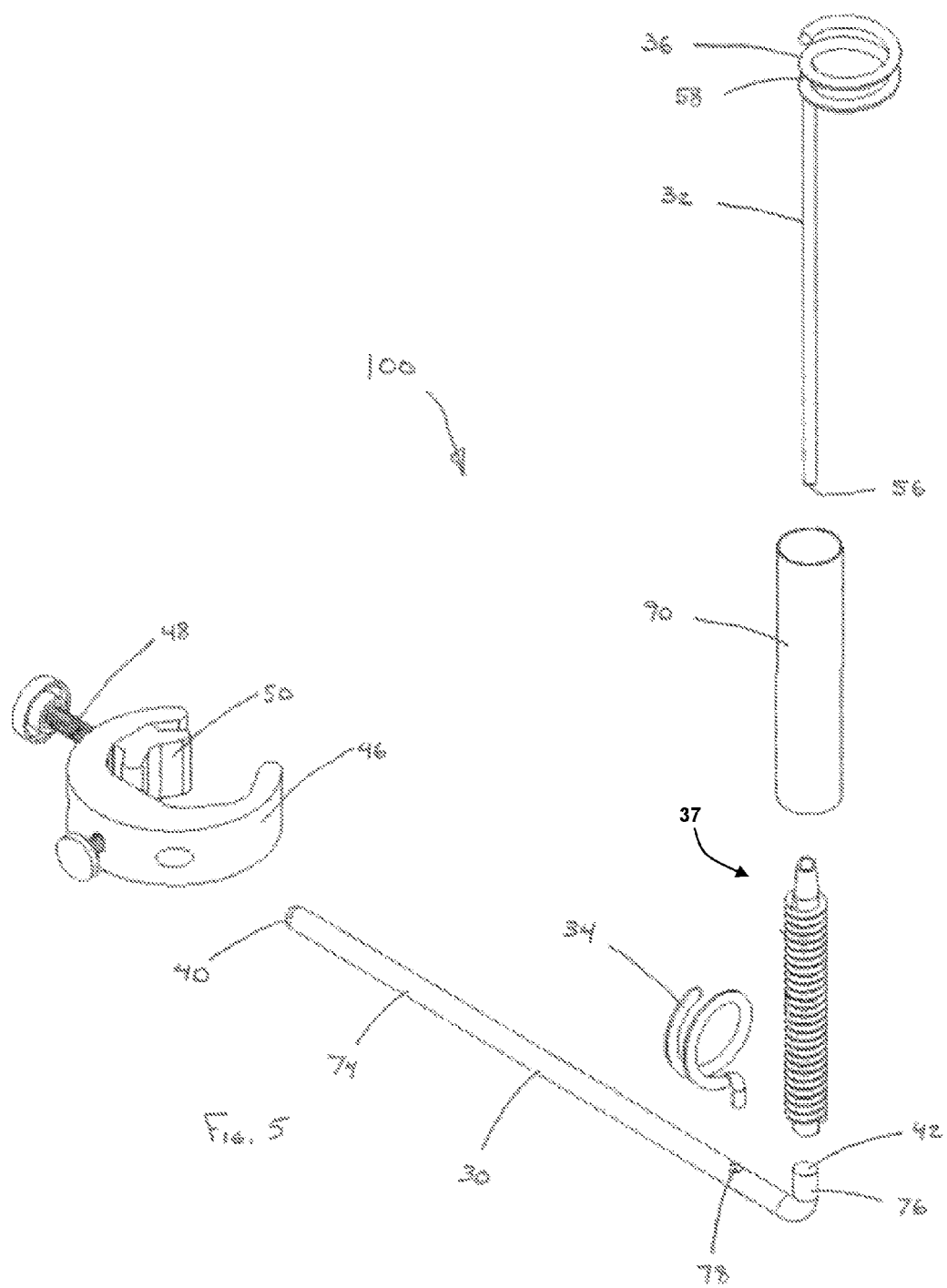

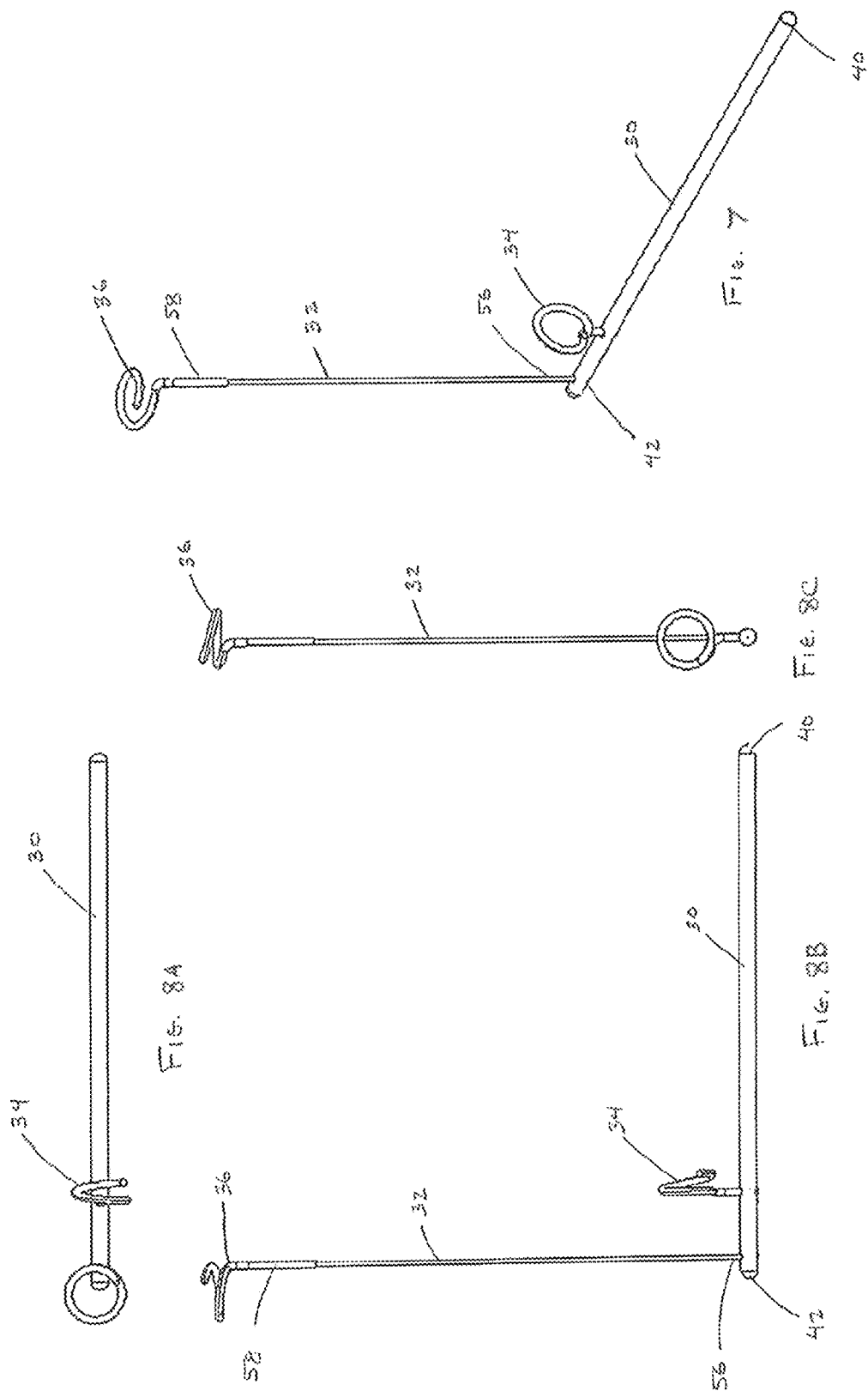

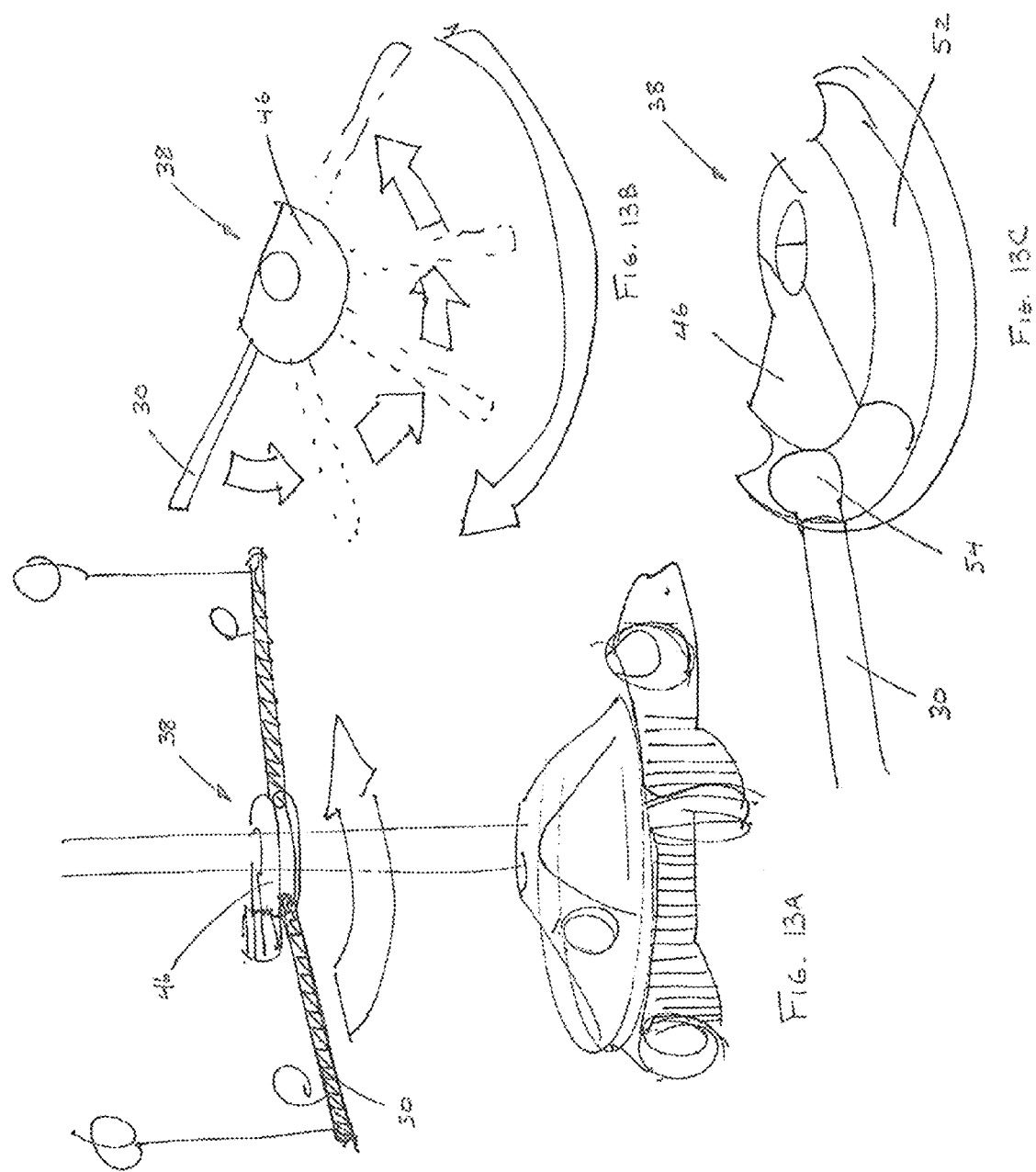

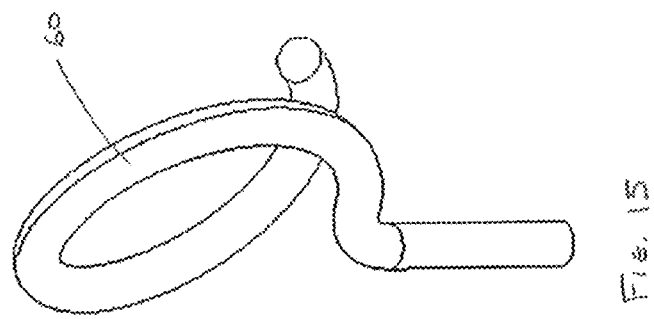
Fig. 15
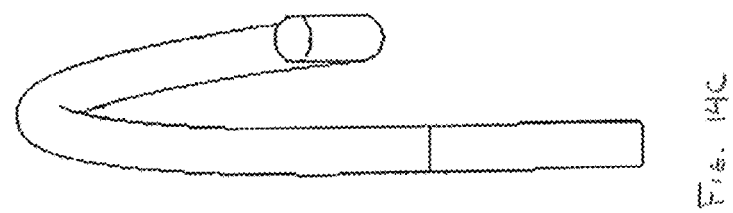
Fig. 14C
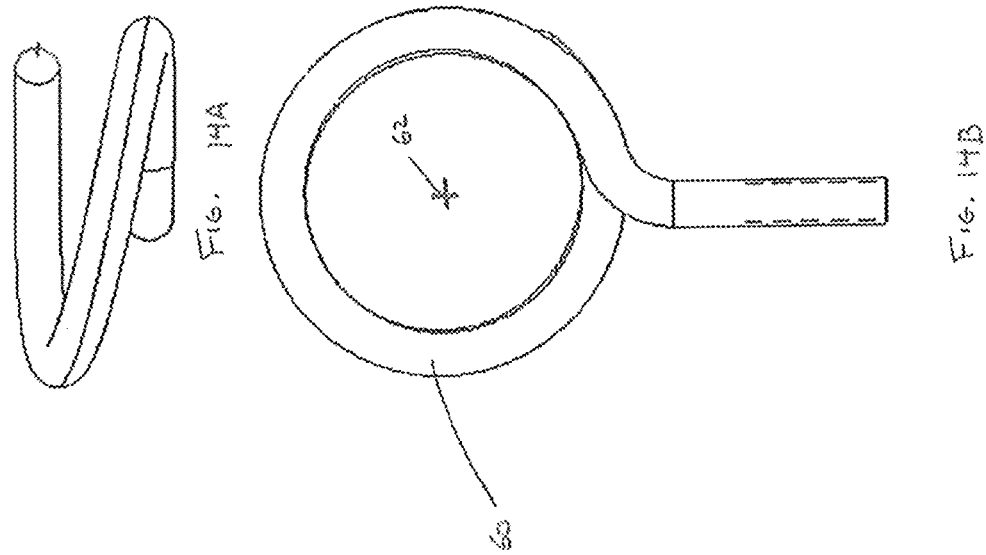
Fig. 14A
Fig. 14B

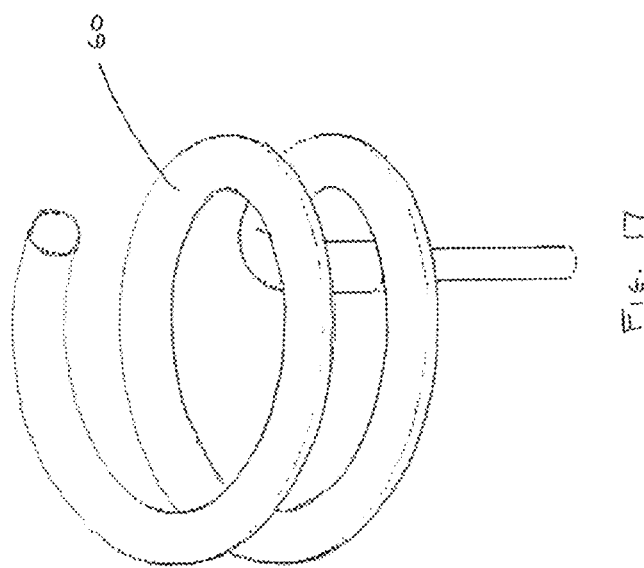
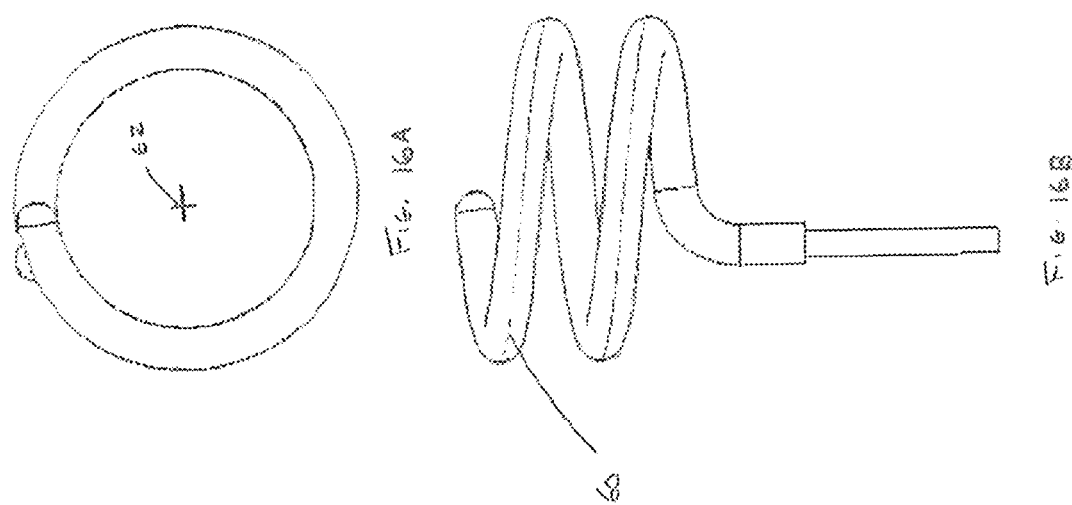

INTRAVENOUS LINE LIFTER DEVICES, SYSTEMS AND METHODS

RELATED APPLICATION

This application claims the benefit of U.S. Provisional Application 61/981,567, filed Apr. 18, 2014, which is hereby incorporated by reference in its entirety.

TECHNICAL FIELD

The present disclosure relates generally to intravenous (IV) lines, and more particularly to holders for minimizing contact of one or more IV lines with the floor or other surfaces.

BACKGROUND

IV lines are typically small and flexible plastic tubes used to transfer fluids from a source into an IV needle or catheter that is positioned in the vein of a medical patient. Intravenous infusions may include fluids to provide hydration or nutrition, and/or medications such as IV antibiotics or IV chemotherapy.

There are two categories of IV lines: peripheral and central lines. A peripheral IV line is one in which the needle is inserted through the skin directly into a vein in the hand or arm, often via a port needle. Peripheral IV's are usually used for a short time period (days) and can become easily dislodged from the vein if pulled on or bumped. The second category of IV lines is a central line. Central lines are IV catheters that are surgically threaded into a large vein leading to the heart, are semi-permanent, and are used for longer term therapies (weeks to years). Central lines provide a secure IV access but also have a risk of becoming infected, which can be serious and life-threatening.

When a patient is in the hospital and receiving intravenous therapy, ambulation is often needed to maintain the patient's health, strength, and endurance. Because it is only possible for an IV line to deliver one fluid at a time, multiple IV lines may necessarily be attached to the patient depending on the number of fluids the patient needs at any given time. When multiple IV lines are attached concurrently to a patient, the IV lines often become tangled, causing nurses to spend valuable time attempting both to untangle the lines and to maintain the lines in an untangled state.

For young children or those having short stature, this problem is further complicated as the discrepancies between the patient's height, IV pump and stand height, and the IV tubing length often result in the IV tubing laying or dragging on the floor and becoming a tripping hazard, or being run over by the IV pole. When this happens the exterior surfaces of the IV tubing may be inadvertently contaminated, and that contamination can be transferred to the patient, for example, by touching or handling the IV tubing, or by placement of the IV tubing next to the patient in bed, which is a common practice. Having dirt, organisms, or other contaminants on the exterior of the tubing makes the immuno-compromised patient at increased risk of having a central line-associated bloodstream infection, or other infectious event.

At the same time, a certain amount of slack is required in the IV lines. Without this slack a patient would be severely limited in mobility or in danger of toppling the IV stand or pole. Additionally, the absence of slack in the IV lines can contribute to separation of the IV tubes from the patient or IV pump, or damage to the patient or patient care equipment. For this reason, shortening the IV lines, or coiling the lines to remove excess slack for the purpose of reducing contamination, is not a viable option.

What is needed in the industry is a mechanism for keeping one or more IV lines suspended for the purpose of reducing contact with the floor, while at the same time permitting temporary slack in the one or more IV lines when the patient moves and slack is desired.

SUMMARY

In one embodiment, the present disclosure provides an IV line device, system, and method for lifting, holding, and managing the slack that is present in an IV line between a patient and patient care equipment for the purpose of keeping tubing of the IV line from contacting the floor and becoming contaminated and entangled in itself, other IV lines, or other medical equipment. Additionally, this device, system, and method permits flexibility in accommodating movement of the patient by allowing temporary slack in the IV line when slack is desired or needed, while at the same time reducing the likelihood of accidental port needle de-accessing and patient falls where the IV line presents a potential trip hazard.

In one embodiment, the IV line device, system, and method can be useful in the pediatric clinical setting for inpatient and outpatient children, such as those ages one to ten years or more, who have an IV (peripheral or central line) attached to an IV pump and are ambulatory. In some embodiments, between one and twelve or more IV lines can be accommodated simultaneously. Some embodiments are fully adjustable to accommodate patients of different sizes, as well as different needs of the patient.

In some embodiments, through its generally smooth surfaces and simple construction, and/or construction that contain no hidden components, crevasses or areas, embodiments of the system and device lend themselves to ease in cleaning and disinfection. Further, all construction materials can be compatible with standard hospital cleaning and disinfecting protocols.

In one embodiment, the present disclosure provides an intravenous line lifter system for supporting one or more IV lines that extend between a patient and patient care equipment. The system includes a first elongated support member, a second elongated support member, and at least two line retention devices. The first elongated support member is configured to have a first end and a second end. The first end of the first elongated support member is selectively couplable to a support for the patient care equipment. The second elongated support member is configured to have a first end and a second end. A portion of the second elongated support member proximal the first end of the second elongated support member is fixedly coupled to the first elongated support member. The first line retention device is coupled to the first elongated support member between the first and second ends of the first elongated support member, while the second line retention device is coupled to the second elongated support member proximate the second end of the second elongated support member.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 5 is an exploded perspective view of the intravenous line lifter device of FIG. 1.

FIG. 7 is a perspective view of an intravenous line lifter device in accordance with an embodiment of the disclosure wherein the second elongated support member is at least partially flexible.

FIG. 8A is a top view of the intravenous line lifter device of FIG. 7.

FIG. 8B is a profile view of the intravenous line lifter device of FIG. 7.

FIG. 8C is an end view intravenous line lifter device of FIG. 7.

FIG. 13A is a perspective view of a swiveling clamp in accordance with an embodiment of the disclosure.

FIG. 13B is a top view of the clamp of FIG. 13A.

FIG. 13C is a close up perspective view of the clamp of FIG. 13A.

FIG. 14A is a top view of a spiraling hook in accordance with an embodiment of the disclosure.

FIG. 14B is a side view of the spiraling hook of FIG. 14A.

FIG. 14C is an end view of the spiraling hook of FIG. 14A.

FIG. 15 is a perspective view of the spiraling hook of FIG. 14A.

FIG. 16A is a top view of a spiraling hook in accordance with an embodiment of the disclosure.

FIG. 16B is a side view of the spiraling hook of FIG. 16A.

FIG. 19 is a perspective view of the spiraling hook of FIG. 18A.

Figure 1:
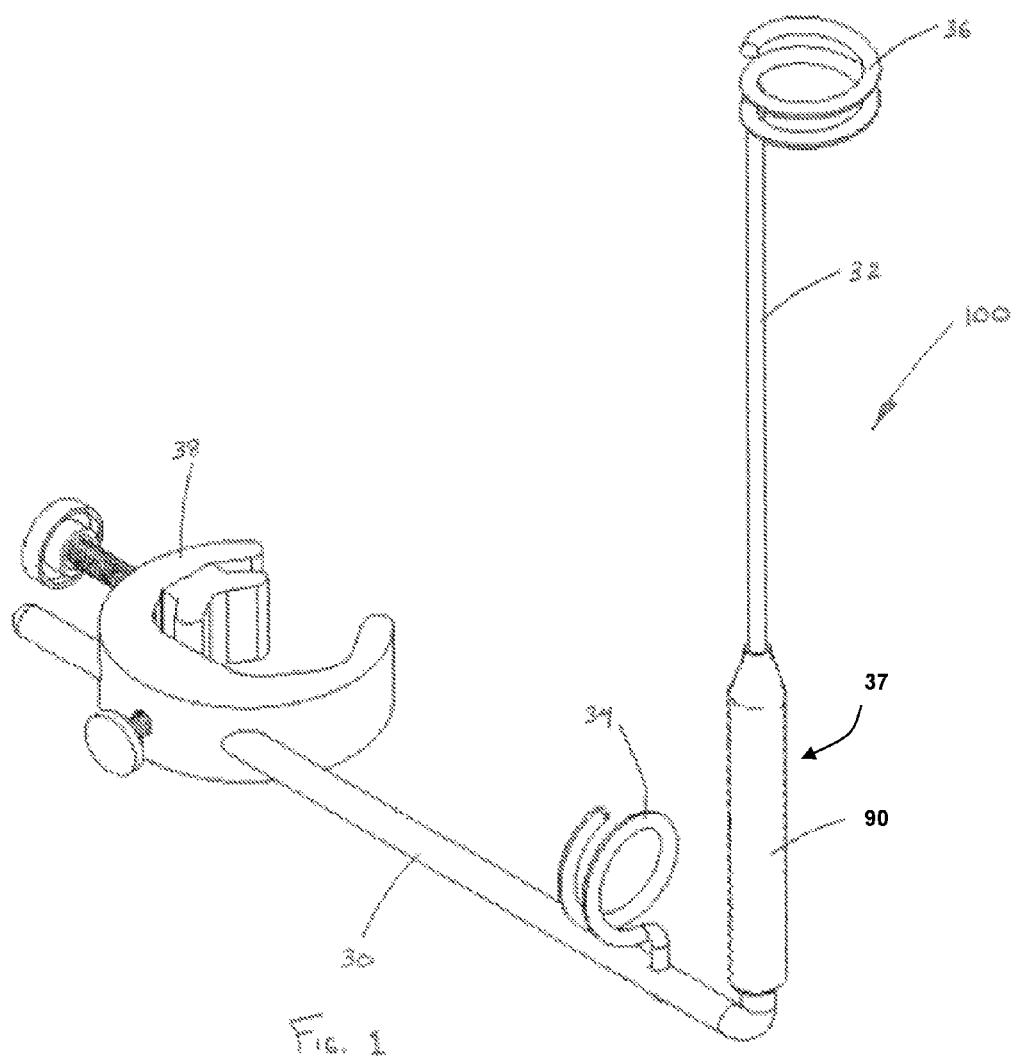
FIG. 1 is a perspective view of an intravenous line lifter device in accordance with an embodiment of the disclosure.
Figure 2:
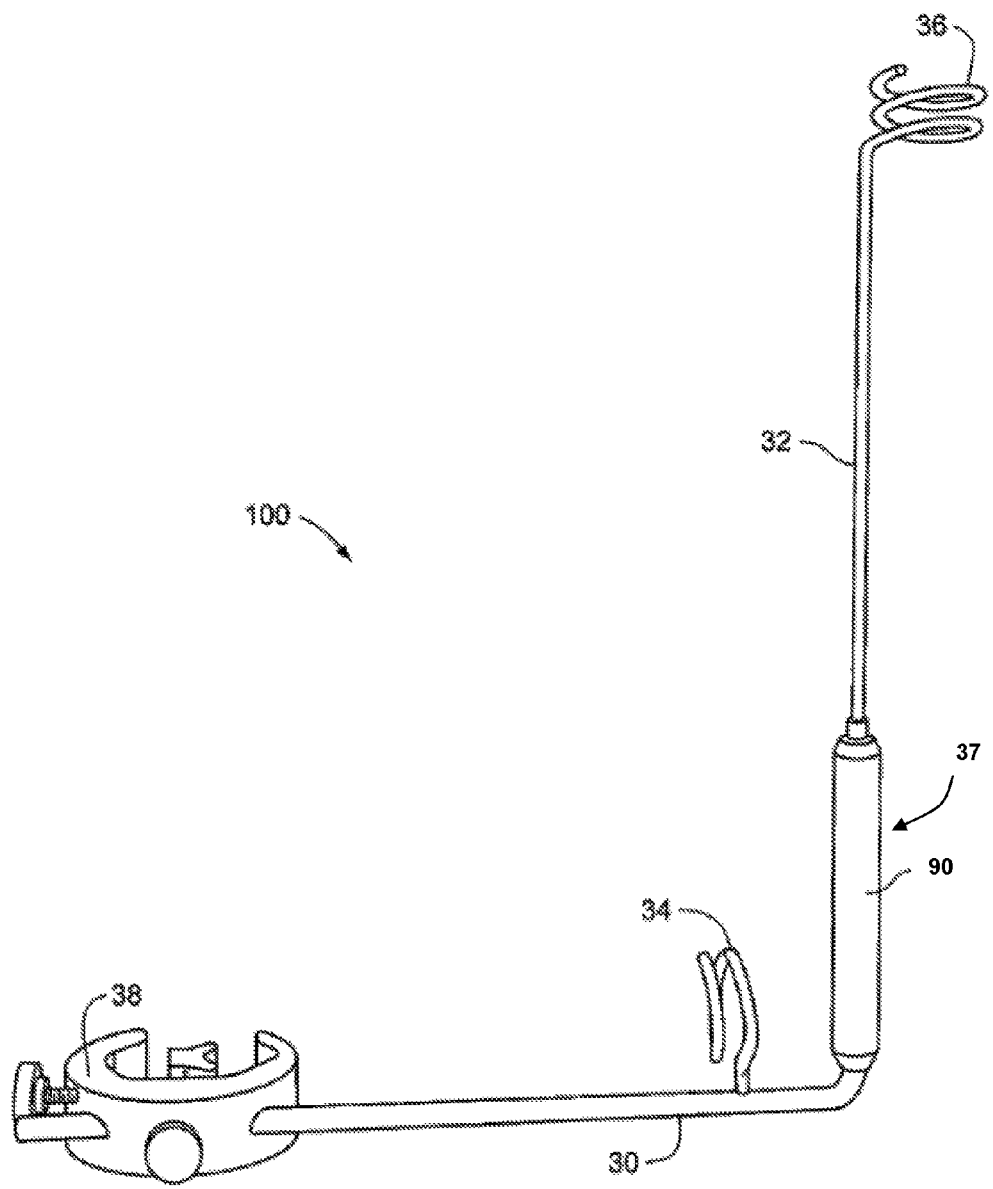
FIG. 2 is a perspective view of the intravenous line lifter device of FIG. 1.
Figure 3:
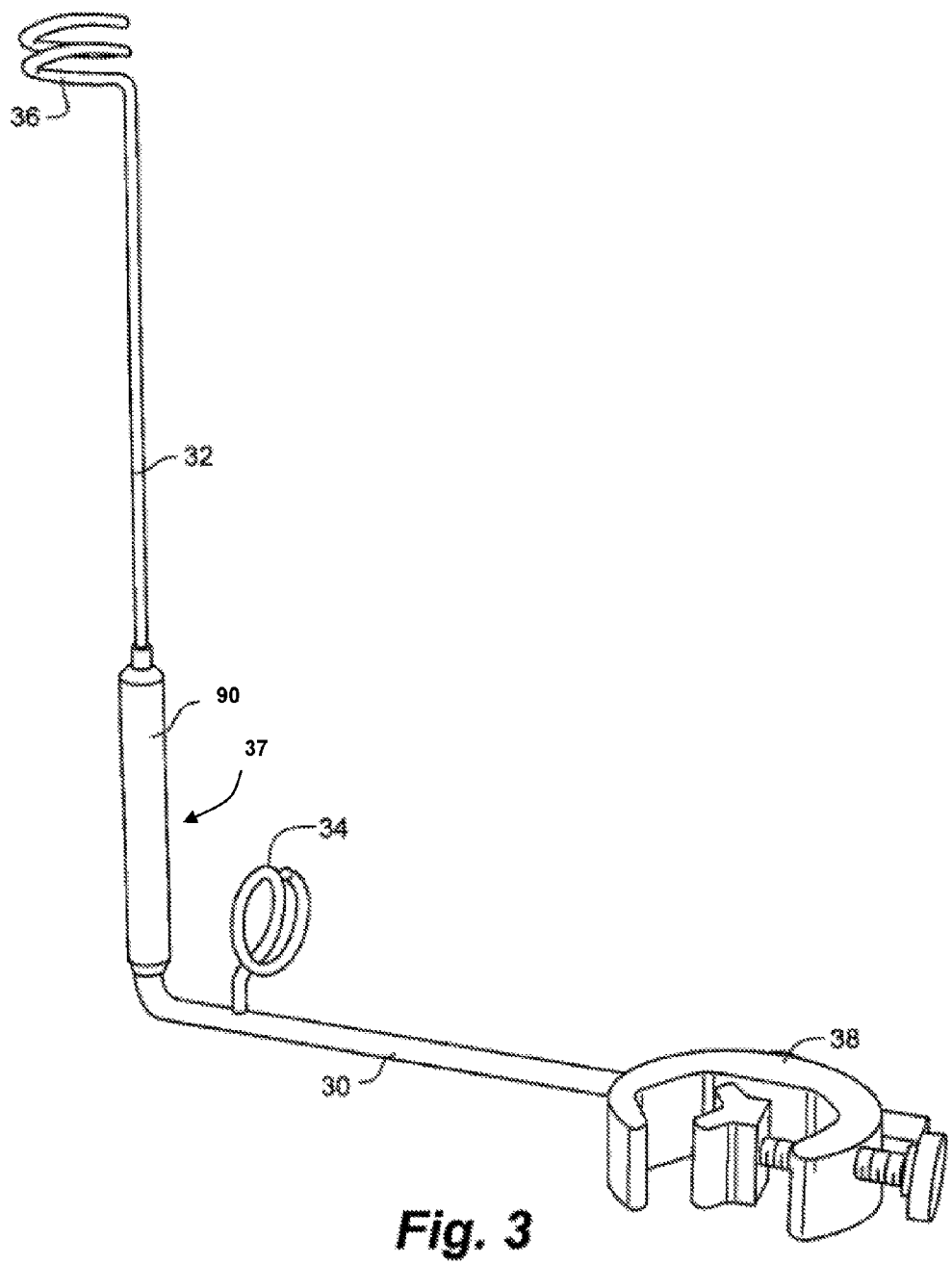
FIG. 3 is a perspective view of the intravenous line lifter device of FIG. 1.
Figure 4:
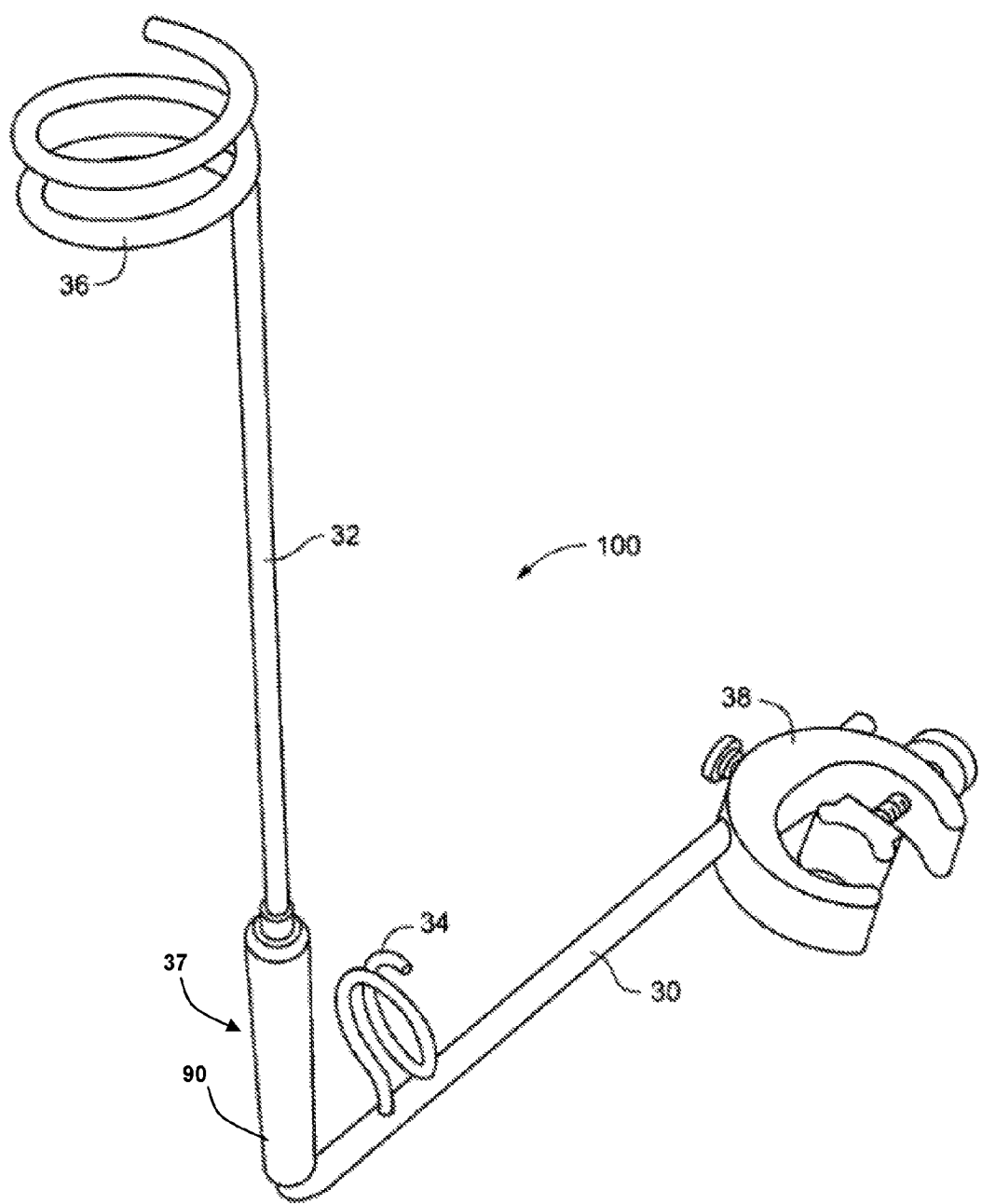
FIG. 4 is a perspective view of the intravenous line lifter device of FIG. 1.

While embodiments are amenable to various modifications and alternative forms, specifics thereof have been shown by way of example in the drawings and will be described in detail. It should be understood, however, that the intention is not to be limited to the particular embodiments described. On the contrary, the intention is to cover all modifications, equivalents, and alternatives falling within the spirit and scope of the appended claims.

DETAILED DESCRIPTION

Referring to FIGS. 1-5, an intravenous line lifter device 100 according to a disclosed and example embodiment is depicted. Intravenous line lifter device 100 generally includes a first elongated support member 30, a second elongated support member 32, a first line retention device 34, and a second line retention device 36. In one embodiment, second elongated support member 32 can further include a flexible joint 37, such as a spring-loaded joint or hinge. In some embodiments, intravenous line lifter device 100 can include clamp 38 for selectively coupling the intravenous line lifter device 100 to patient care equipment 92.

Referring to FIG. 5, in one embodiment, first elongated support member 30 has a first end 40 and a second end 42. In one embodiment, first elongated support member 30 can be constructed of a substantially rigid or semi-rigid material. For example, first elongated support member 30 can be constructed of stainless steel, aluminum, fiberglass, plastic, another material, or a composite of materials. In one embodiment, first elongated support member 30 can have a surface that lends itself to easy cleaning and disinfection.

In one embodiment, first elongated support member 30 can be in the form of a cylindrical rod. In one embodiment, first elongated support member 30 can be substantially straight. In another embodiment, first elongated support member 30 can have a proximal portion 74 defining a longitudinal axis angularly displaced relative to a longitudinal axis defined by a distal portion 76 of first elongated support member 30. In one embodiment, distal portion 76 can be substantially orthogonal to proximal portion 74.

First elongated support member 30 can include a bore 78, configured to receive attachments, for example first line retention device 34. Bore 78 can be a through bore that transversely passes entirely through first elongated support member 30, or bore 78 can be a blind bore. In one embodiment, bore 78 can be threaded.

Figure 6A:
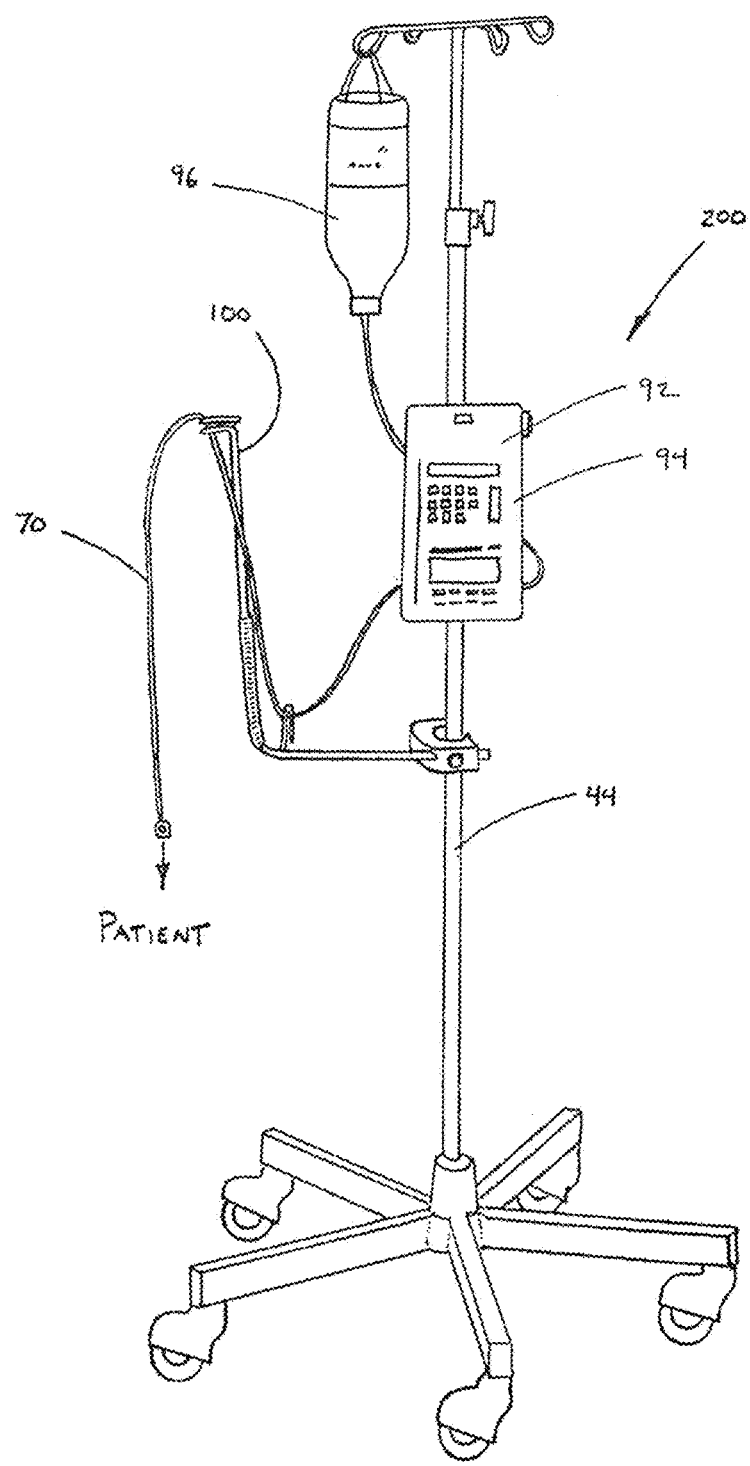
FIG. 6A is a perspective view of an intravenous line lifter system in accordance with an embodiment of the disclosure, wherein the intravenous line lifting system is in a relaxed position.
Figure 6B:
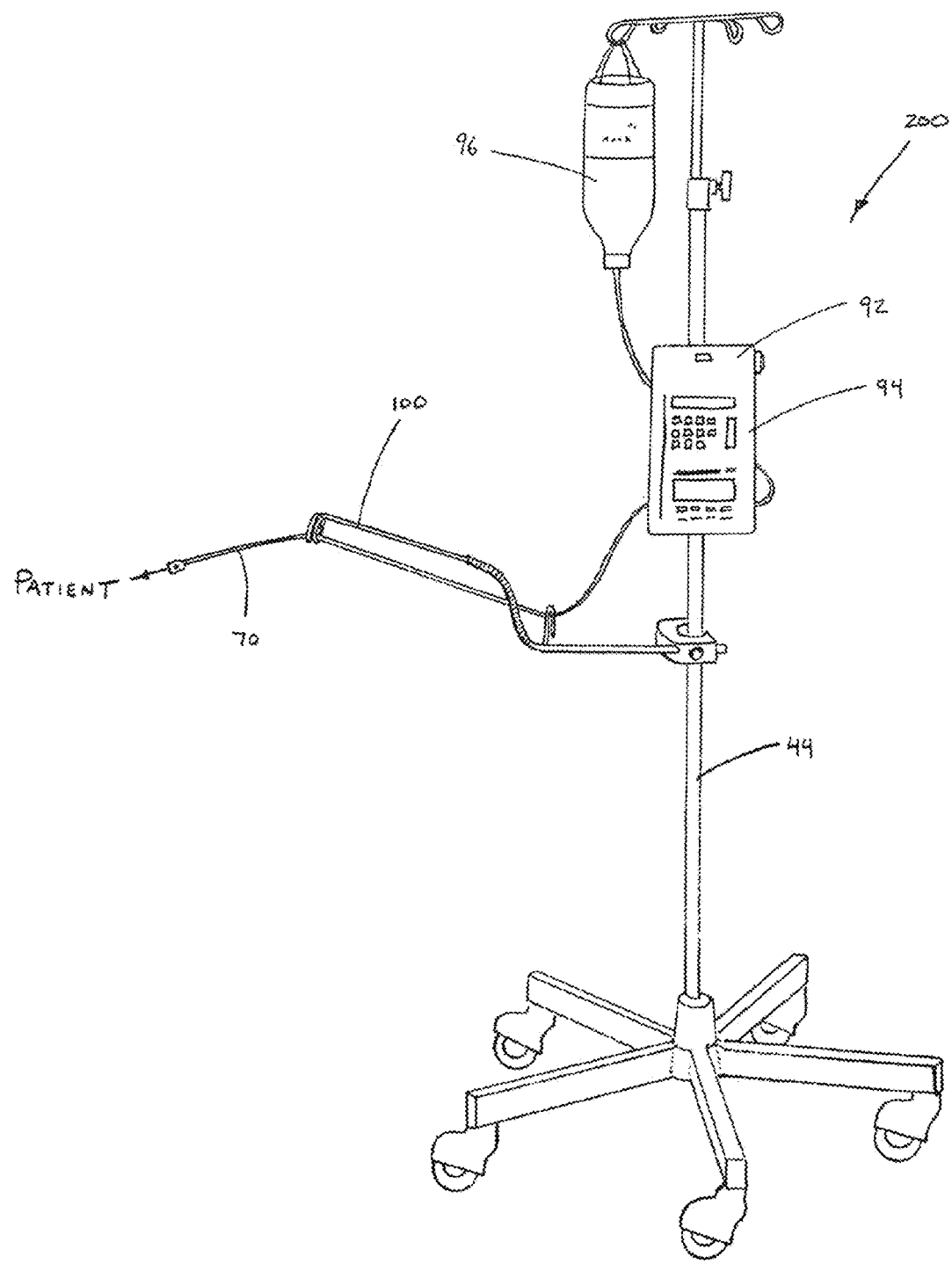
FIG. 6B is a perspective view of the intravenous line lifter system of FIG. 6A, wherein the intravenous line lifting system is in a flexed position.
Figure 9B:
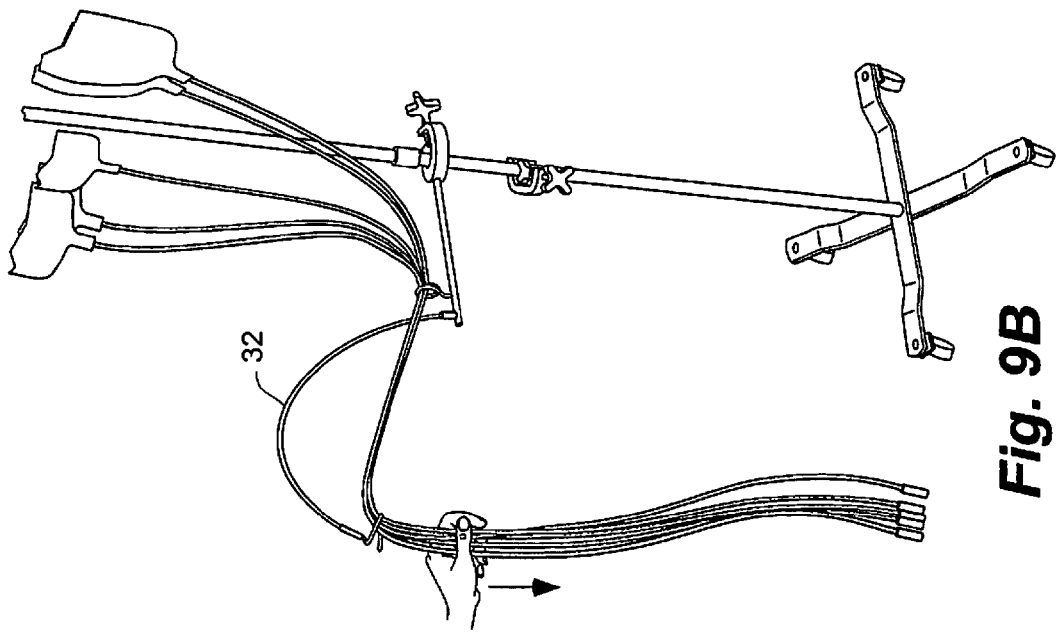
FIG. 9B is a perspective view of the intravenous line lifter system of FIG. 9A, wherein the intravenous line lifting system is in a flexed position.
Figure 9A:
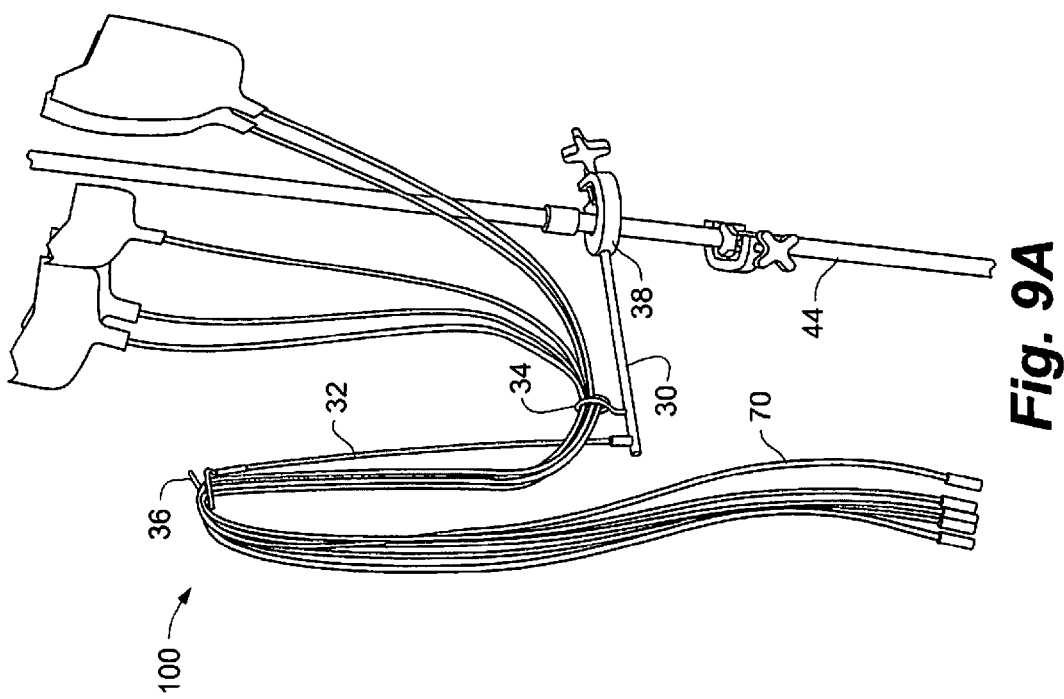
FIG. 9A is a perspective view of an intravenous line lifter system in accordance with an embodiment of the disclosure, wherein the intravenous line lifting system in a relaxed position.
Figure 10B:
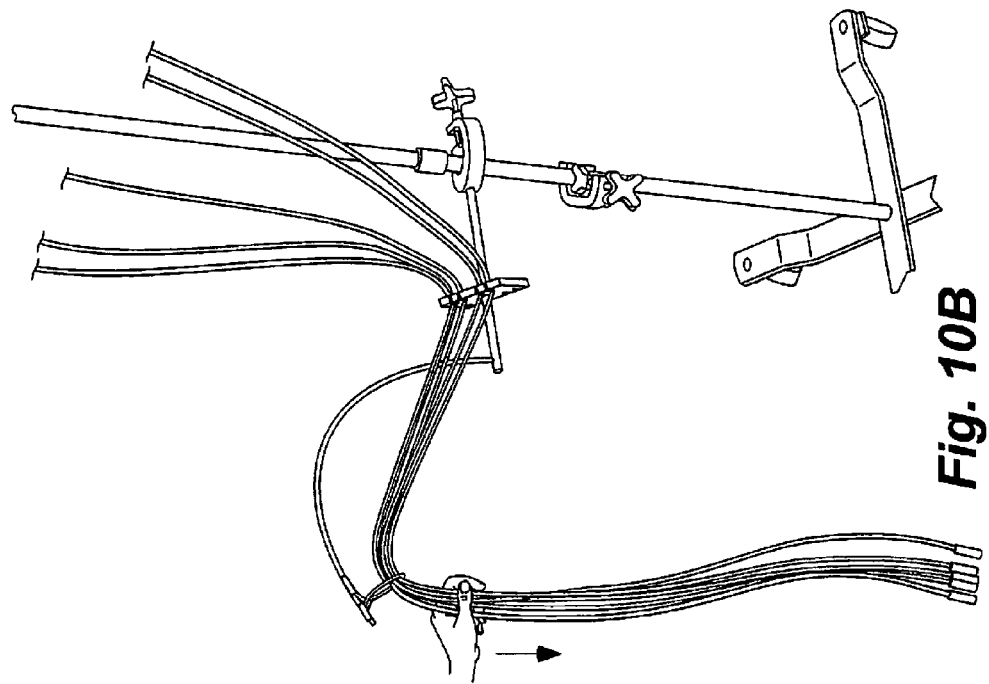
FIG. 10B is a perspective view of the intravenous line lifter system of FIG. 10A, wherein the intravenous line lifting system is in a flexed position.
Figure 10A:
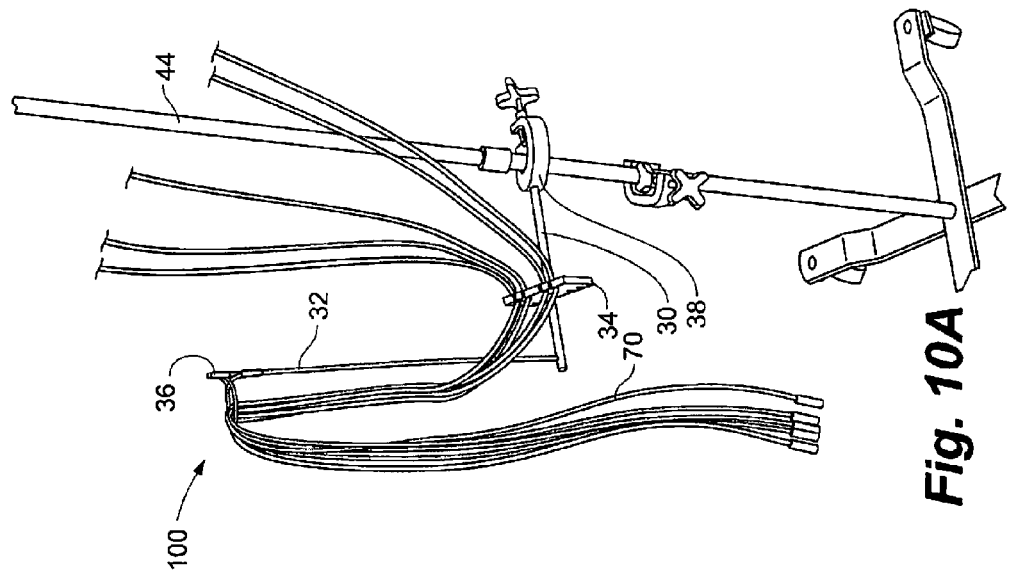
FIG. 10A is a perspective view of an intravenous line lifter system in accordance with an embodiment of the disclosure including alternative line retention devices, wherein the intravenous line lifter system is in a relaxed position.

Referring to FIGS. 6A and 6B, which depict an intravenous line lifting system 200 according to a disclosed and example embodiment, first elongated support member 30 is selectively couplable to patient care equipment 92, or a support 44 for patient care equipment 92. For example, first elongated support member 30 can be attached to an IV pole support 44 so that first elongated support member 30 extends radially outward from support 44 in a substantially horizontal manner. In one embodiment, for patient care equipment 92 equipment can include one or more medical infusion pumps 94, one or more medicament containers 96, and one or more IV lines 70. In other embodiments, first elongated support member 30 can be coupled to a hospital bed, wheelchair, cart, or wagon.

In one embodiment, first elongated support member 30 can be coupled to support 44 in a manner that allows the radial extension of first elongated support member 30 to be lengthened or shortened as needed. In one embodiment, first elongated support member 30 can be telescoping, segmented, or otherwise constructed in a manner in which its length of configuration can be altered or adjusted in use or for storage.

Figure 11:
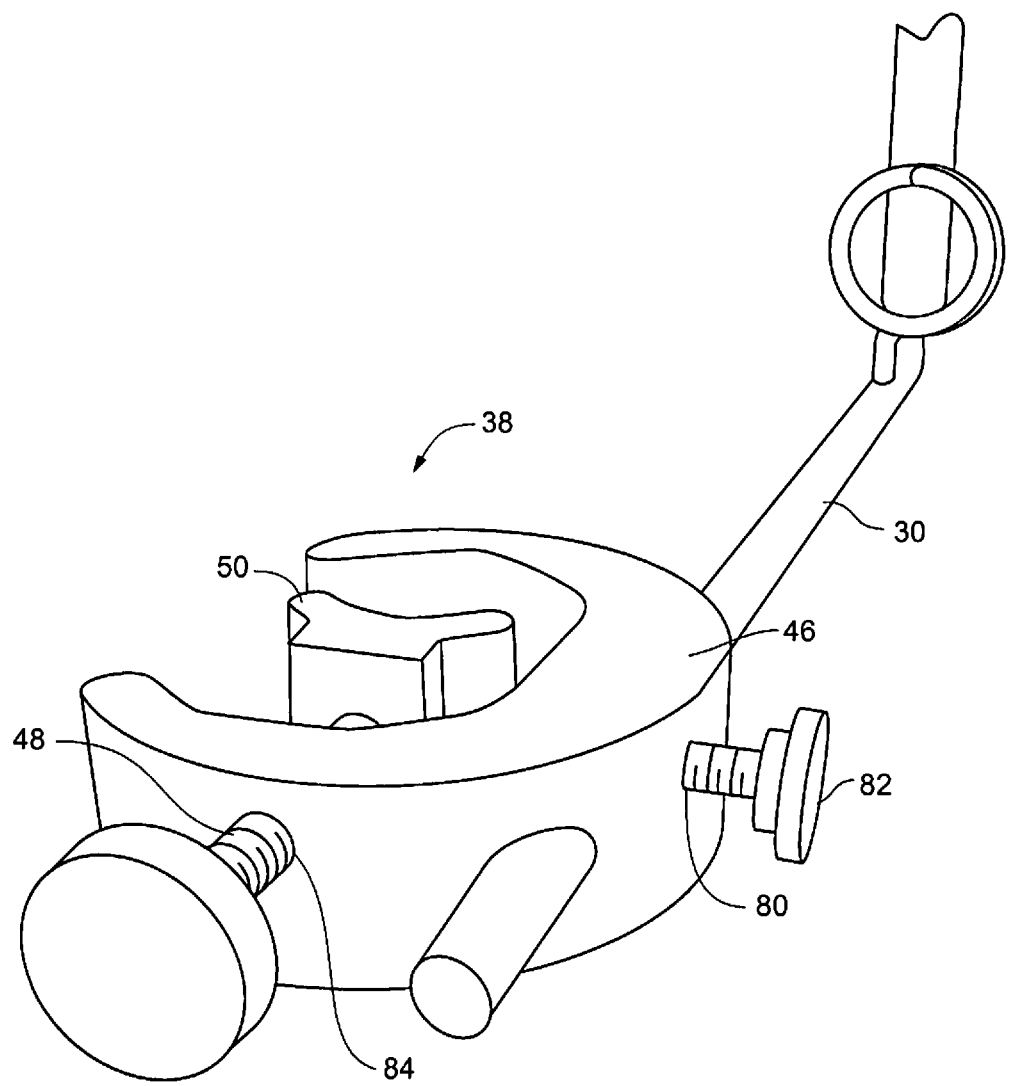
FIG. 11 is a perspective view of a clamp in accordance with an embodiment of the disclosure.
Figure 12:
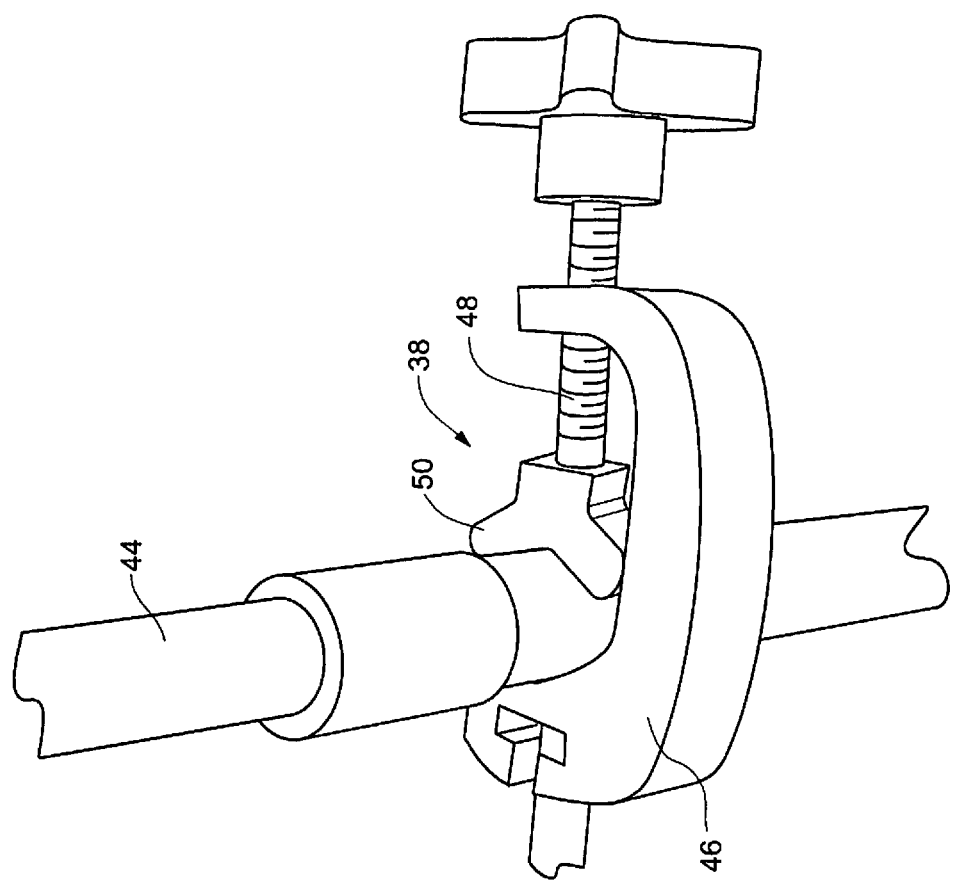
FIG. 12 is a perspective view of a clamp in accordance with an embodiment of the disclosure.

Referring to FIGS. 11 and 12, in one embodiment, clamp 38 can be a C-clamp. In one embodiment, clamp 38 can be comprised of a clamp body portion 46 and a threaded portion 48, wherein threaded portion 48 is threadedly coupled to body portion 46 via bore 84. Threaded portion 48 can include a support engaging surface 50, wherein threaded portion 48 and support engaging surface 50 can be positioned relative to clamp body portion 46 for coupling clamp 38 to support 44. Clamp 38 can be constructed of aluminum, stainless steel or another material or composite of materials to allow easy cleaning and disinfection. Numerous other configurations and constructions of clamp 38 can be used in other embodiments, with the embodiments of FIGS. 11-12 being but one example.

In one embodiment, clamp 38 can be configured to allow a portion of first elongated support member 30 to pass therethrough, thereby allowing first elongated support member 30 to be coupled to support 44 in a manner that allows the radial extension of first elongated support member 30 to be lengthened or shortened relative to support 44 as needed. In one embodiment, clamp 38 can further include a threaded bore 80 for receiving a set screw 82 configured to apply a frictional force against first elongated support member 30 for the purpose of holding first elongated support member 30 in a fixed position relative to clamp 38.

In some embodiments, first elongated support member 30 is fixed in position relative to clamp body portion 46. Referring to FIGS. 13A-C, in other embodiments first elongated support member 30 can move relative to clamp body portion 46 and swivel or pivot about support 44 by moving along a track, rail or other structure 52 defined in or on clamp body portion 46. In this embodiment, first end 40 can be defined as a ball 54 slidable along track 52. In one embodiment, first elongated support member 30 can pivot about 180 degrees or more relative to support 44.

In other embodiments, first elongated support member 30 can be coupled to support 44 by a cam lock, screw lock, rotational bearing attachment, frictional attachment, some other attachment device, or a combination of any of the forgoing attachment mechanisms or devices. In one embodiment, first elongated support member 30 or second elongated support member 32 can be folded or collapsed relative to support 44 when not in use or when extra slack in IV lines 70 is not needed or desired.

Referring again to FIG. 5, in one embodiment, second elongated support member 32 has a first end 56 and a second end 58. In one embodiment, second elongated support member 32 can be constructed of a substantially rigid or semi-rigid material. For example, second elongated support member 32 can be constructed of stainless steel, aluminum, fiberglass, plastic, another material, or a composite of materials. In one embodiment, first elongated support member 30 can have a surface that lends itself to easy cleaning and disinfection.

In one embodiment, the portion of second elongated support member 32 proximal first end 56 is coupled to first elongated support member 30. In one embodiment, second elongated support member 32 is coupled proximate the first elongated support member second end 42. In one embodiment, second elongated support member 32 can be coupled to first elongated support member 30 via flexible joint 37. For example, flexible joint 37 can be a spring-loaded joint or hinge, such as a coil spring hingedly coupling first elongated support member 30 to second elongated support member 32.

In one embodiment, flexible joint 37 can be fixedly coupled to first elongated support member 30 and second elongated support member 32. For example, flexible joint 37 can be welded or soldered to first elongated support member 30 and second elongated support member 32. In other embodiments, first elongated support member 32 can be coupled to first elongated support member 30 in a variety of ways, including but not limited to a press fitting, a threaded connection, via a set screw, an adhesive bond, a separate joining member, a strain relief connection, another suitable device or connector, or a combination of any of the forgoing attachment devices or connectors. In one embodiment, a protective sheath 90, such as a heat shrink wrap or another suitable material, for example neoprene, can at least partially surround flexible joint 37 to allow easy cleaning and disinfection and prevent contamination of, pinch points and other interactions with flexible joint 37 in use.

In another embodiment, second elongated support member 32 can be constructed of a flexible material that is able to recoil or spring back into position or shape after bending. FIGS. 7-10B depict various embodiments of an intravenous line lifter device 100 according to a disclosed and example embodiment wherein the second elongated support member is at least partially flexible. For example, in one embodiment, second elongated support member 32 can be constructed of fiberglass or a similar material or composite to allow resilience, while at the same time permitting easy cleaning and disinfection. In an alternative embodiment, resilient member can be constructed of spring steel, plastic or another material or composite of materials.

In another embodiment, the joint between second elongated support member 32 and first elongated support member 30 can be foldable or adjustable. In another embodiment, second elongated support member 32 can be telescoping. In yet another embodiment, second elongated support member 32 can include a rigid portion and a flexible portion. In one embodiment, rigid portion and flexible portion can be constructed of different materials.

Referring again to FIGS. 1-5, in one embodiment, first line retention device 34 is coupled to first elongated support member 30 between the first end 40 and second end 42, though the particular position at which device 34 is coupled to member 32 can vary from that depicted. First line retention device 34 can be coupled to first elongated support member 30 by any of the methods described in connecting first elongated support member 30 to second elongated support member 32. Additionally, first line retention device 34 can be welded to first elongated support member 30, or integrally formed in, on or with first elongated support member 30. In one embodiment, first line retention device 34 can be removably or adjustably coupled to first elongated support member 30 via bore 78.

In one embodiment, second line retention device 36 can be coupled to second elongated support member 32 proximate second elongated support member second end 58. In one embodiment, second line retention device 36 can be integral molding into second elongated support member 32. In another embodiment, second line retention device 36 can be configured to snuggly fit over second elongated support member second end 58. In some embodiments, second line retention device 36 can be affixed to second elongated support member second end 58 by adhesive. In other embodiments, any of the previously describe methods of connection can be used, for example, second line retention device 36 can be removably, or adjustably coupled to second elongated support member 32.

Figure 17:
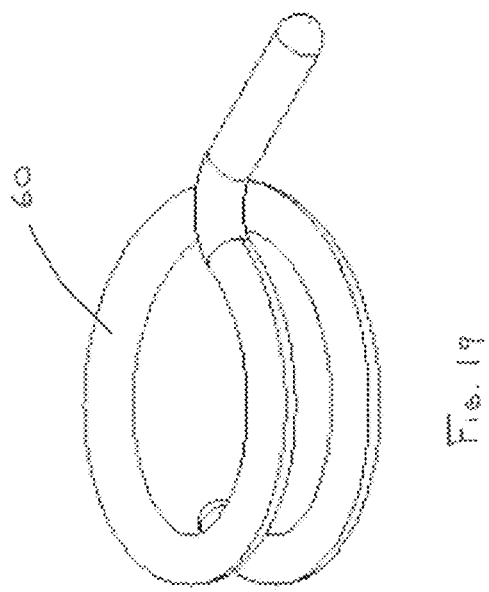
FIG. 17 is a perspective view of the spiraling hook of FIG. 16A.
Figure 18A:
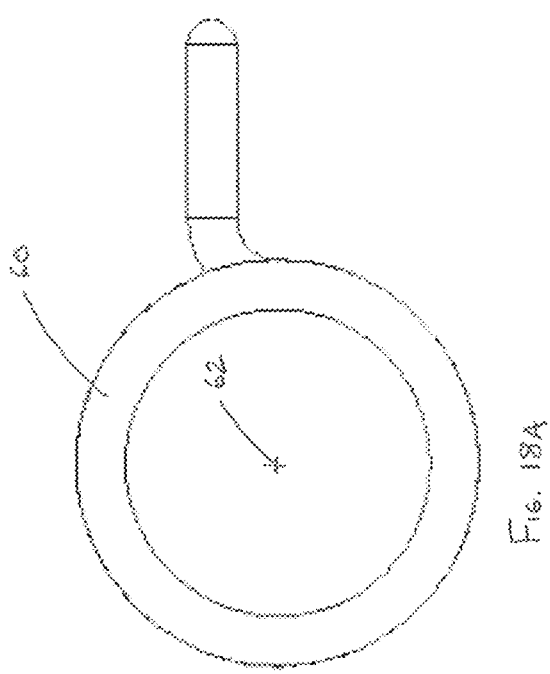
FIG. 18A is a top view of a spiraling hook in accordance with an embodiment of the disclosure.
Figure 18B:
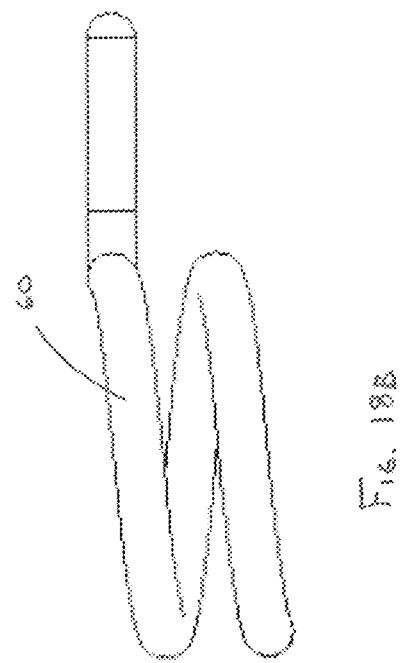
FIG. 18B is a side view of the spiraling hook of FIG. 18A.

In some embodiments, either or both line retention devices 34 and 36 can be in the form of a bridle ring or spiraling hook. Referring to FIGS. 14A-15, in one embodiment, spiraling hook 60 can circumscribe center point 62 one time. Referring to FIGS. 16A-17, in another embodiment, spiraling hook 60 can circumscribe center point 62 two times. In other embodiments, spiraling hook 60 can circumscribe center point 64 any number of times, including fractions. For example, as depicted in FIGS. 18A-19, spiraling hook 60 can circumscribe center point 62 one and a half times. In one embodiment, spiraling hook 60 can circumscribe center point 62 in a circular fashion. In another embodiment, spiraling hook 60 can be configured in a D-shape when viewed from the top. In one embodiment, spiraling hook 60 can have an opening oriented in a direction facing first elongated support member 30, second elongated support member 30, or any other direction that is advantageous to operation or retention of the IV lines 70.

In other embodiments, either or both of line retention devices 34 and 36 can comprise a carabiner or similar structure with spring-loaded gates or latches that enable easy insertion and removal of IV tubing while retaining the tubing therein during use. In one embodiment, line retention devices 34 and/or 36 also can comprise or interface with an S-clip or other device or structure that can facilitate more thorough securement of tubing in line retention devices 34 and/or 36.

In one embodiment, line retention devices 34 and 36 can be constructed of aluminum, stainless steel or another material or composite of materials to allow easy cleaning and disinfection. In another embodiment, line retention devices 34 and 36 can be constructed of a malleable material to allow for adjustment and customization. In another embodiment, line retention devices 34 and 36 can include individual tracks or recesses for each IV line 70. In another embodiment, line retention devices 34 and 36 can have a rubber, plastic or other coating, or a surface texture or treatment, to either increase or reduce friction with IV tubing therein or provide an aesthetic or other benefit.

Figure 20:
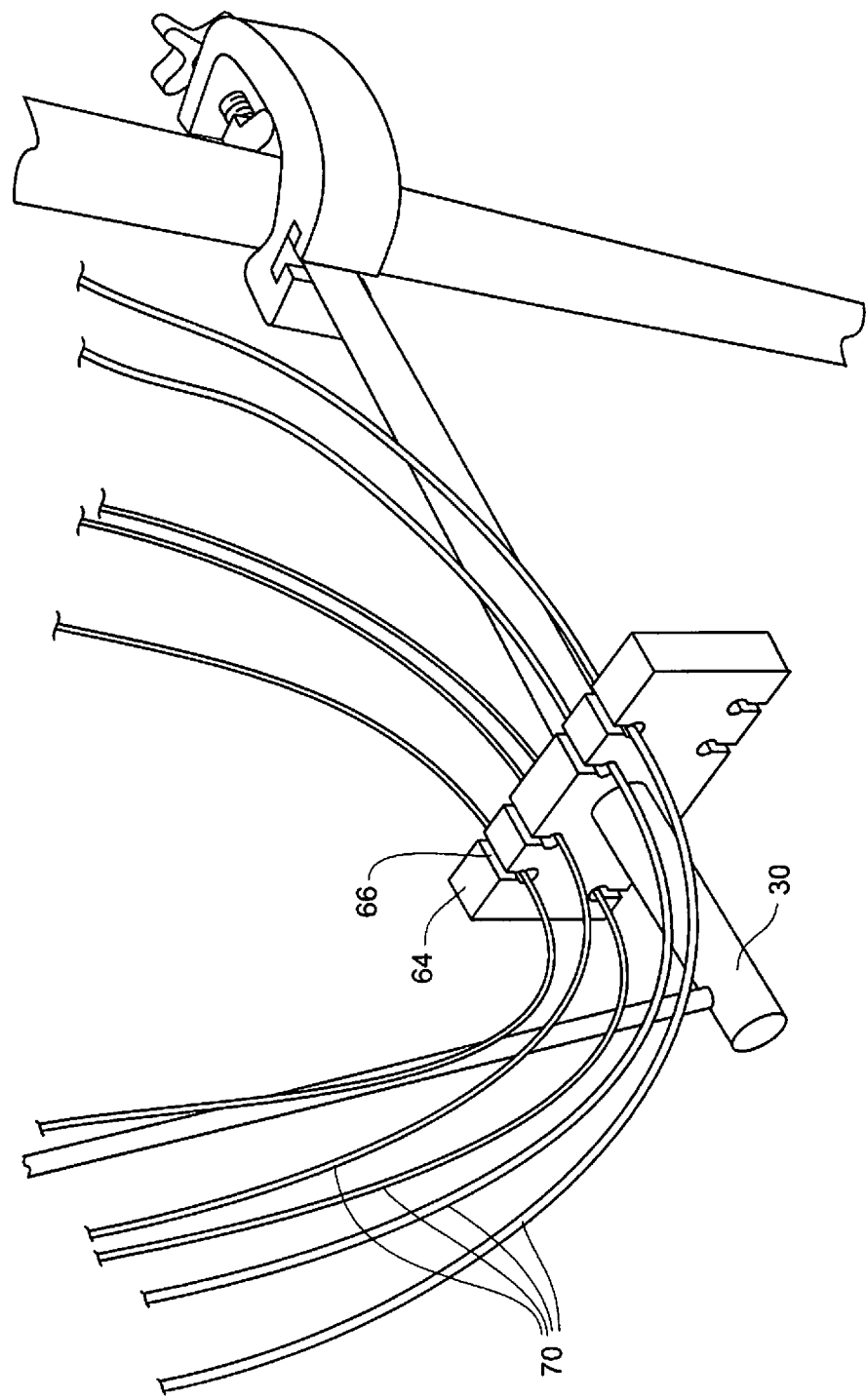
FIG. 20 is a perspective view of a tube holder in accordance with an embodiment of the disclosure.

Referring to FIG. 20, in another embodiment, either or both line retention devices 34 and 36 can be in the form of a tube holder 64. In one embodiment, tube holder 64 can be defined by a plurality of notches 66 sized to accept one or more IV lines 70. Numerous other configurations and constructions of tube holder 64 can be used in other embodiments, with the embodiment of FIG. 20 being but one example. In one embodiment, tube holder 64 can be resilient. For example, tube holder 64 can be constructed of foam or a similar material. In some embodiments, tube holder 64 is selectively couplable to or positionable on first elongated support member 30 or second elongated support member 32. In another embodiment, tube holder 64 can be integrally molded into first elongated member 30 or second elongated member 32. In one embodiment, tube holder 64 can be used in place of, or in addition to, first line retention device 34 and/or second line retention device 36.

Figure 21:
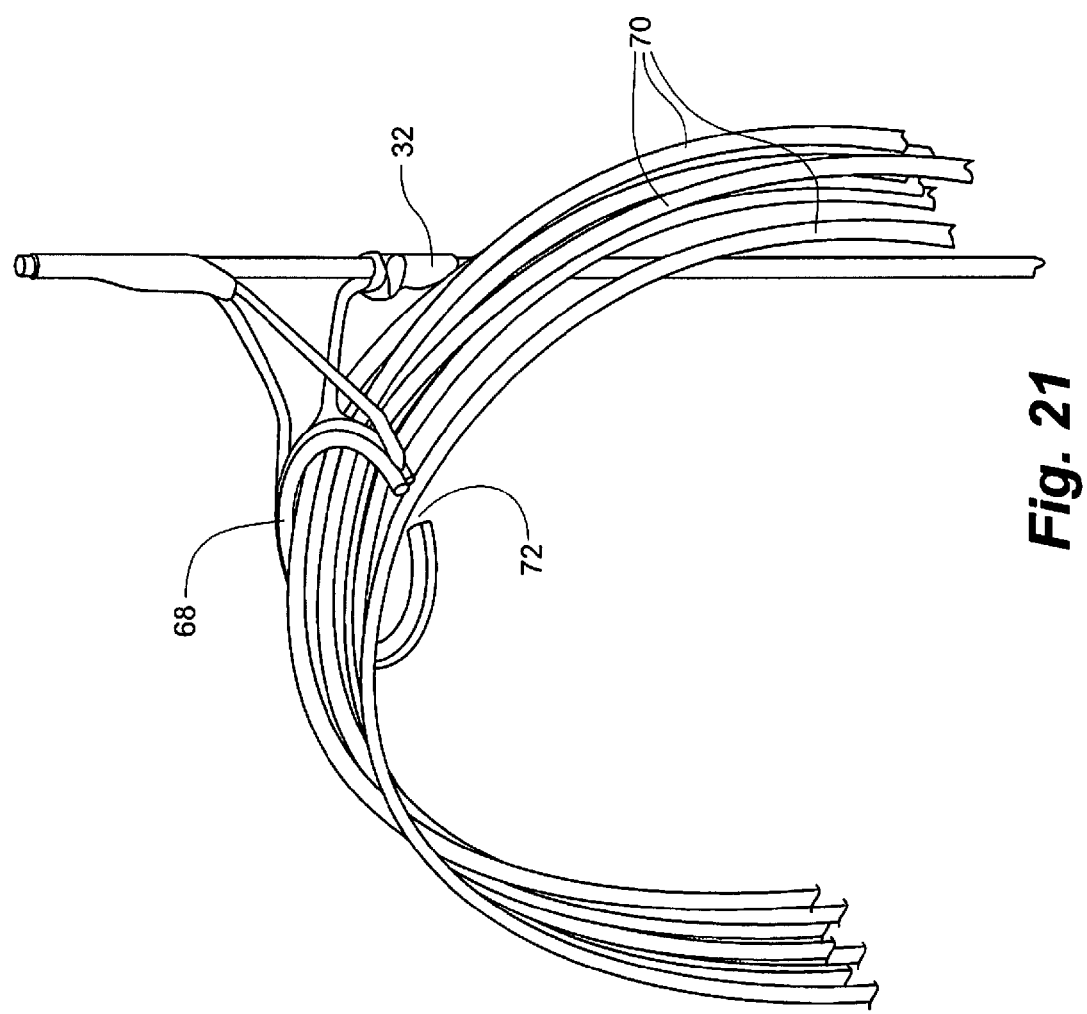
FIG. 21 is a perspective view of a split ring in accordance with an embodiment of the disclosure.

Referring to FIG. 21, in another embodiment, either or both line retention devices 34 and 36 can be in the form of split ring 68. A split 72 defined in split ring 68 can be sized to allow only a single IV line 70 to pass at a given time or configured such that split ring 68 must be temporarily deformed in order for IV line 70 to pass in or out of split 72. In one embodiment, split 72 can be oriented in a direction facing first elongated support member 30, resilient elongated support member 30, or any other direction that is advantageous to operation or retention of the IV lines 70.

In one embodiment, intravenous line lifter device 100 and/or system 200 can interact with or include other devices beyond IV lines 70 and patient care equipment 92. In one embodiment, intravenous line lifter device 100 and/or system 200 can comprise a holder or other device to accommodate a patient controlled analgesia (PCA), timer, schedule, electronic or paper chart, or other device in easy access to the patient. In still other embodiments, intravenous line lifter device 100 and/or system 200 can accommodate a name tag, label, protective bumper or padding, decorative covering or logo, toy, novelty or other item a patient or medical professional may desire to customize device 100 and/or system 200.

In operation, the IV lines traversing from the patient care device to the patient are threaded through the first line retention device 34 and second line retention device 36 in the interim. When the patient is in close proximity to support 44, the second elongated support member, of which the second line retention device 36 is coupled, suspends the IV lines, thereby minimizing any contact of the IV lines with the floor or other surfaces. When the patient moves away from support device 44, second elongated support member 32 flexes relative to first elongated support member 30 to provide slack to the patient without stressing the IV tubing connections on patient care device or patient. The direction of flexing can vary with the direction of movement of the patient. When either the patient moves back towards support 44, or the support 44 is moved toward the patient, second elongated support member 32 returns to a non-flexed or relaxed position.

Line lifter device 100 is shown in connection with the suspension of IV lines, but is not restricted to medical applications. Line lifter device 100 can be utilized with electrical or other cords, cables or tubes (e.g., those associated with computers, household or commercial grade appliances including hairdryers and other styling or cosmetic tools, irons, vacuums, and kitchen appliances, among myriad others), as well as pneumatic or hydraulic lines in other applications. Moreover, line lifter device 100 is not limited to the specific configuration of the embodiments shown. The various components of line lifter device 100 can be assembled in reverse order, such that second line retention device 36 is near to the ground for line or cord management purposes.

In one embodiment, line lifter device 100 can come in a range of sizes and configurations and can include colors (e.g., by colored materials, coatings, anodizing, etc.) and other aesthetic features. In any embodiment, line lifter device 100 can further comprise one or more bumpers or pads (not depicted) on the ends of first elongated support member 30 or resilient elongated support member 32 to prevent injury from inadvertent contact.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of embodiments.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. An intravenous line lifter system for supporting one or more IV lines that extend between a patient and patient care equipment, the intravenous line lifter system comprising:
   a first elongated support member having a first end and a second end, wherein the first elongated support member is selectively couplable to a support for the patient care equipment;
   a second elongated support member having a first end and a second end, wherein the first end of the second elongated support member is permanently fixedly coupled to the second end of the first elongated support member;
   a first line retention device coupled to the first elongated support member between the first and second ends of the first elongated support member; and
   a second line retention device coupled to the second elongated support member proximate the second end of the second elongated support member.

2. The system of claim 1, further comprising a clamp capable of selectively coupling the first elongated support member to the support for the patient care equipment.

3. The system of claim 2, wherein the clamp comprises a c-clamp.

4. The system of claim 2, wherein the clamp is configured to allow the selective coupling of the first elongated support member to the support for the patient care equipment at multiple points along a length of the first elongated support member between the first end and the second end of the first elongated support member.

5. The system of claim 1, wherein a portion of the second elongated support member proximate the first end of the second elongated support member comprises a flexible coupling.

6. The system of claim 5, wherein the flexible coupling comprises a coil spring.

7. The system of claim 5, wherein the coil spring is at least partially covered by a protective sheath.

8. The system of claim 1, wherein the first elongated support member and the second elongated support member are substantially rigid.

9. The system of claim 1, wherein the second line retention device comprises a bridle ring.

10. The system of claim 9, wherein the second line retention device is integrally molded into second elongated support member.

11. An intravenous line lifting system comprising:
    a clamp configured to selectively couple to a support structure;
    a first elongated support member having a first end and a second end, wherein the first elongated support member is selectively coupleable to the clamp;
    a second elongated support member having a first end and a second end, wherein the first end of the second elongated support member is permanently fixedly coupled to the second end of the first elongated support member;
    a first line retention device coupled to the first elongated support member between the first and second ends of the first elongated support member; and
    a second line retention device coupled to the second elongated support member proximate the second end of the second elongated support member.

12. The system of claim 11, wherein the clamp is configured to selectively couple to a support structure comprising an IV pole.

13. The system of claim 12, wherein the clamp comprises a c-clamp.

14. The system of claim 12, wherein the clamp is configured to selectively couple the first elongated support member to the support structure at multiple points along a length of the first elongated support member between the first end and the second end of the first elongated support member.

15. The system of claim 11, wherein the second elongated support member comprises a flexible portion proximate the first end of the second elongated support member.

16. The system of claim 15, wherein the flexible coupling comprises a coil spring.

17. The system of claim 16, wherein the coil spring is at least partially covered by a protective sheath.

18. The system of claim 11, wherein the first elongated support member and the second elongated support member are substantially rigid.

19. The system of claim 11, wherein the first line retention device and the second line retention device comprise bridle rings.

20. The system of claim 19, wherein the second line retention device is integrally molded into second elongated support member.

* * * * *